United States Patent
Webber et al.

(10) Patent No.: US 6,616,614 B2
(45) Date of Patent: Sep. 9, 2003

(54) APPARATUS AND METHOD FOR ASCERTAINING CARDIAC OUTPUT AND OTHER PARAMETERS

(75) Inventors: Margaret R. Webber, Los Altos, CA (US); Jeffrey J. Christian, San Jose, CA (US); Harry D. Nguyen, Anaheim, CA (US); Vladimir J. Drbal, Belmont, CA (US)

(73) Assignee: Keimar Corporation, Los Altos, CA (US)

( * ) Notice: Subject to any disclaimer, the term of this patent is extended or adjusted under 35 U.S.C. 154(b) by 0 days.

(21) Appl. No.: 09/956,064

(22) Filed: Sep. 18, 2001

(65) Prior Publication Data

US 2003/0055353 A1 Mar. 20, 2003

(51) Int. Cl.[7] ............................ A61B 5/02
(52) U.S. Cl. ............ 600/526; 600/345; 600/348; 600/364
(58) Field of Search ............... 600/526, 364, 600/585, 345, 348; 604/164.01–164.09

(56) References Cited

U.S. PATENT DOCUMENTS

| | | | | |
|---|---|---|---|---|
| 3,905,888 A | * | 9/1975 | Mindt et al. ............. 204/415 |
| 4,015,600 A | * | 4/1977 | Liautaud ................. 604/177 |
| 4,221,567 A | * | 9/1980 | Clark et al. .............. 436/68 |
| 4,819,655 A | * | 4/1989 | Webler .................... 600/526 |
| 4,874,500 A | | 10/1989 | Madou et al. |
| 4,919,141 A | * | 4/1990 | Zier et al. ............... 600/345 |
| 5,322,063 A | * | 6/1994 | Allen et al. .............. 600/347 |
| 5,409,666 A | * | 4/1995 | Nagel et al. ............. 422/82.07 |
| 5,651,767 A | * | 7/1997 | Schulman et al. ........ 604/8 |
| 5,788,647 A | * | 8/1998 | Eggers ................... 600/526 |
| 5,928,155 A | * | 7/1999 | Eggers et al. ........... 600/526 |
| 5,944,695 A | * | 8/1999 | Johnson et al. ........ 604/164.01 |
| 5,971,934 A | * | 10/1999 | Scherer et al. ......... 600/526 |
| 6,064,900 A | * | 5/2000 | Vadgama et al. ....... 600/345 |

* cited by examiner

Primary Examiner—Robert L. Nasser
Assistant Examiner—Patricia Mallari
(74) Attorney, Agent, or Firm—Dorsey & Whitney LLP (57) ABSTRACT

Apparatus for ascertaining cardiac output of the heart of a patient comprising a control and display module. A venous probe is inserted into a vein in the forearm of the patient and is coupled into the control and display module and provides an electrical signal representing the dissolved oxygen in the venous blood. An arterial probe is inserted into an artery in the forearm of the patient and is coupled into the control and display module and provides an electrical output signal representing the dissolved oxygen in the arterial blood. The control and display module has a visible display that provides a continuous in vivo cardiac output that utilizes an arterial venous oxygen differential equation which includes an adjustment factor for adjusting for venous blood being sampled rather than mixed venous blood in the pulmonary artery of the patient.

15 Claims, 6 Drawing Sheets

APPARATUS AND METHOD FOR ASCERTAINING CARDIAC OUTPUT AND OTHER PARAMETERS

This invention relates to an apparatus and method for ascertaining cardiac output and other parameters of a patient and more particularly to an apparatus and method for ascertaining cardiac output of the heart of a patient and other parameters such as oxygen content, carbon dioxide content, pH, hemoglobin in the blood of the patient, temperature and blood pressure.

Cardiac output measurements have heretofore been made. In the past, such measurements have been made by the use of a thermal dilution pulmonary artery catheter. The use of such thermal dilution pulmonary artery catheters provides an estimate of the true cardiac output and may have inaccuracies ranging from 20% or greater of the true output. It has been found that the use of such thermal dilution catheters increases hospital costs while exposing the patient to potential infectious arrhythmogenic, mechanical and therapeutic misadventure. There is therefore a need for a new and improved apparatus and method for ascertaining cardiac output.

In general, it is an object of the present invention to provide an apparatus and method for ascertaining cardiac output of a patient.

Another object of the invention is to provide an apparatus of the above character which can be utilized for measuring in vivo arterial blood gases.

Another object of the invention is to provide an apparatus of the above character which includes a control module and venous and arterial probes adapted to be coupled into the control module.

Another object of the invention is to provide an apparatus of the above character in which the probes are blunt and atraumatic to the vessel wall.

Another object of the invention is to provide an apparatus of the above character in which the probes are coated with an anti-thrombogenic agent.

Another object of the invention is to provide an apparatus of the above character in which the probes utilized can be used without the use of an IV drip.

Another object of the invention is to provide an apparatus of the above character in which the probes are small and use electrochemical sensors designed for use in the forearm.

Another object of the invention is to provide an apparatus of the above character in which the control module is small and compact so that it can be held in a human hand.

Another object of the invention is to provide an apparatus of the above character in which the control module is provided with a display which can be readily viewed.

Another object of the invention is to provide an apparatus of the above character in which the probes utilized can be disposed of after one time use.

Another object of the invention is to provide an apparatus of the above character which can be economically manufactured.

Additional objects and features of the invention will appear from the following description in which the preferred embodiments are set forth in detail in conjunction with the accompanying drawings.

In general, the apparatus of the present invention for ascertaining cardiac output of the heart of a patient having arteries having arterial blood flow therein supplied by the heart and veins having venous blood therein being returned to the heart, at least certain of the arteries and veins being disposed in the forearm of the patient. The apparatus comprises a control and display module. A venous probe adapted to be inserted into a vein in the forearm of the patient is coupled to the control and display module and provides an electrical signal representing the dissolved oxygen in the venous blood in the vein in which the venous probe is disposed. An arterial probe adapted to be inserted into an artery in the forearm of the patient is coupled into the control and display module and provides an electrical signal representing the dissolved oxygen in the arterial blood in the artery. The control and display module is provided with a display and includes a computer receiving the electrical signals from the venous probe and the arterial probe and provides a continuous in vivo cardio output on the display by utilization of an arterial venous oxygen differential equation which includes an adjustment factor to compensate for the venous blood being sampled in the forearm rather than the mixed venous blood in the pulmonary artery.

Figure 1:
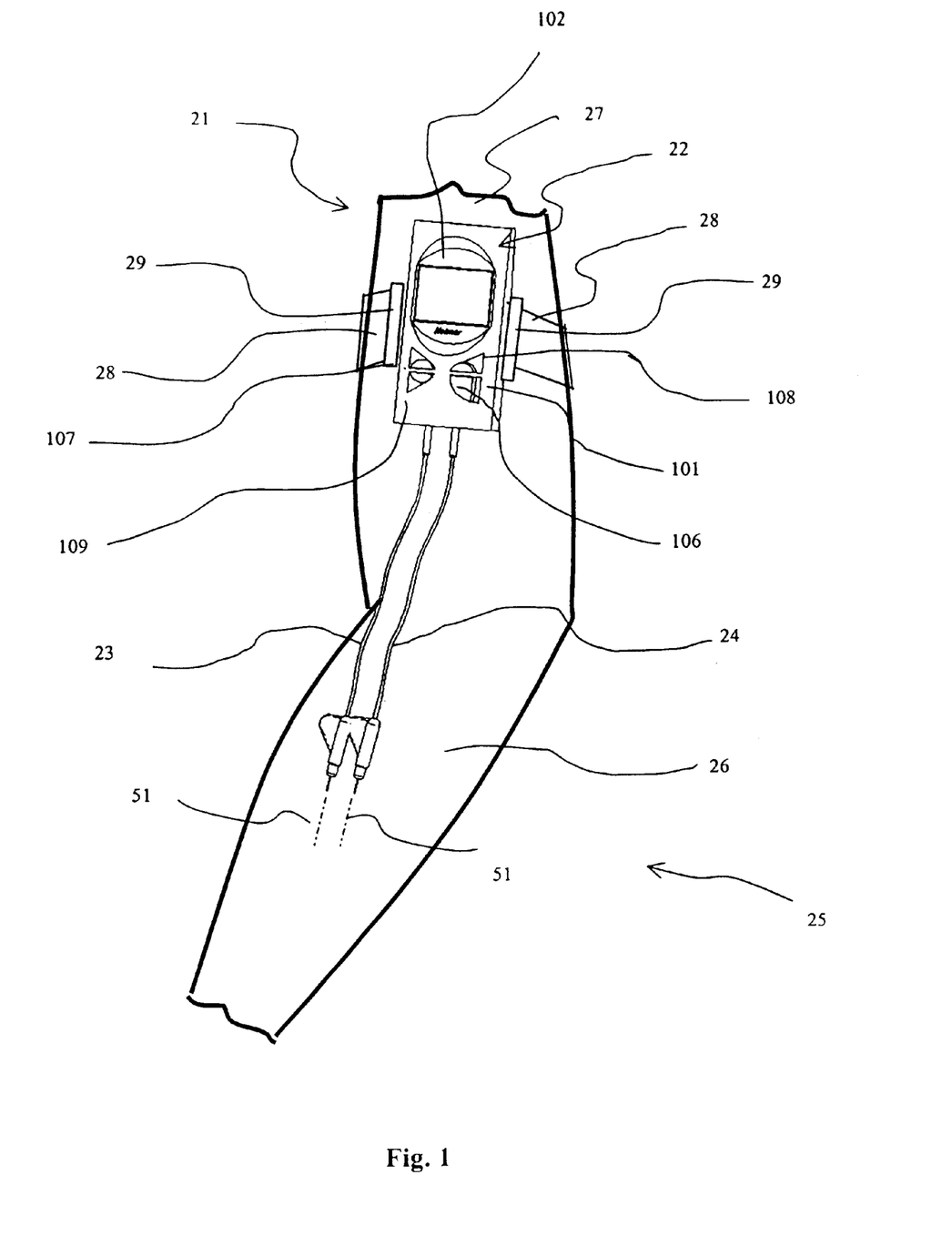
FIG. 1 is an isometric view of an apparatus incorporating the present invention being used in the forearm of a patient and practicing the method of the present invention.
Figure 2:
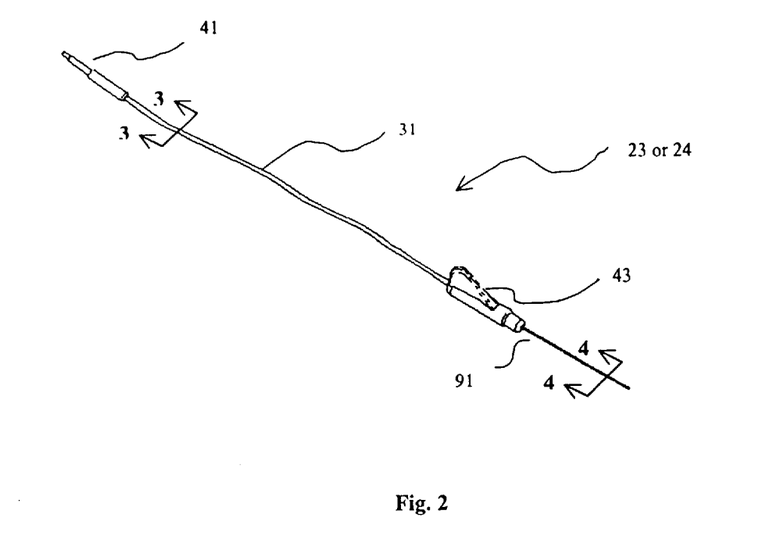
FIG. 2 is an isometric view of one of the probes utilized in the apparatus shown in FIG. 1.
Figure 3:
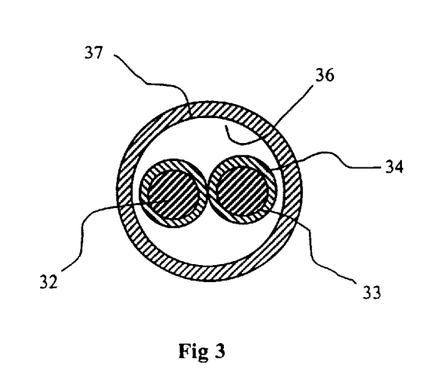
FIG. 3 is an enlarged cross sectional view taken along the line 3—3 of FIG. 2.
Figure 4:
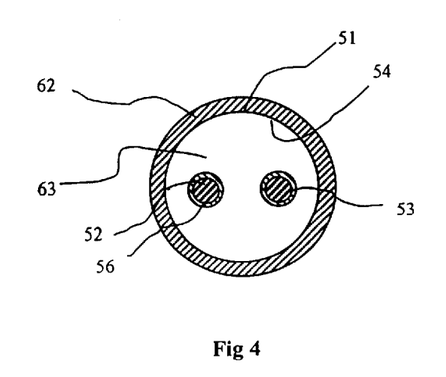
FIG. 4 is an enlarged cross sectional view taken along the line 4—4 of FIG. 2.
Figure 5:
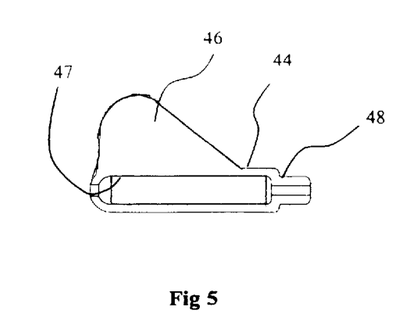
FIG. 5 is an enlarged side elevational view of one half of the winged probe hub shown in FIG. 2.

More in particular, the apparatus 21 for making intra-arterial/intravenous electrochemical measurements of cardiac output, partial oxygen pressure, partial carbon dioxide pressure and pH in blood in vivo in humans is comprised of a control and display module 22 and arterial probes 23 and 24 which are coupled into the control module 22. As hereinafter explained, the apparatus 21 is particularly adapted for use in connection with an arm 25 of the human patient by use of the forearm 26 and upper arm 27. The human patient has a heart and arteries supplied from the heart having arterial blood therein and veins having venous blood therein being returned to the heart. The module 22 can be secured to upper arm 27 by Velcro-type arm bands 28 secured to brackets 29. The arterial and venous probes 23 and 24 are substantially identical. However, they can be appropriately color coded as for example red for the arterial probe and blue for the venous probe.

This oxygen probe is shown more in detail in FIGS. 2 through 7 and as shown therein, such a probe consists of an electrical cable 31 which carries a number of electrical conductors as for example two electrical conductors 32 and 33 covered by insulation 34 and being disposed in a lumen 36 in a sleeve or elongate member 37 formed of a suitable material such as a polymer. An electrical male connector 41 which is connected to the conductors 32 and 33 and is adapted to be inserted into a female electrical connector (not shown) is provided in the control and display module 22. The other end of the cable 31 is mounted in a butterfly-like winged probe hub 43 made of a suitable material such as plastic. The hub 43 as shown can be fabricated in two halves with one half being shown in FIG. 5, with each half being provided with a semi-cylindrical body portion 44 and an upstanding wing portion 46 having a semi-cylindrical longitudinally extending recess 47 therein. An annular recess 48 is formed on the distal end of the body portion 46. When the two halves are brought together, a cap 49 is mounted on the annular recess 48.

Figure 6:
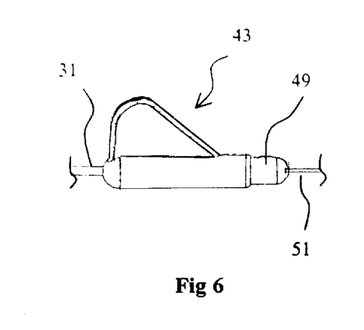
FIG. 6 is an enlarged side elevational view of the winged probe hub shown in FIG. 1.
Figure 7:
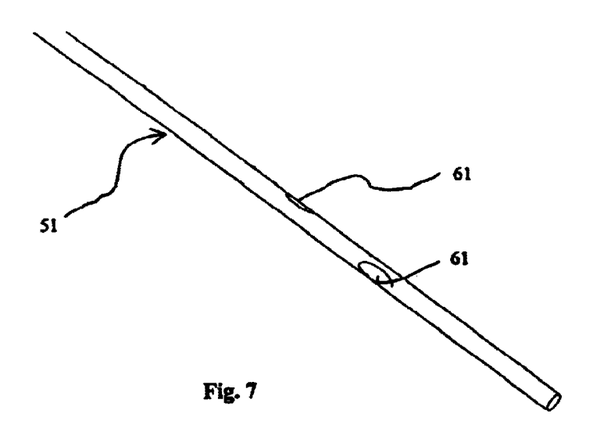
FIG. 7 is an isometric view of a probe incorporating the present invention which can be utilized for measuring other parameters.
Figure 8:
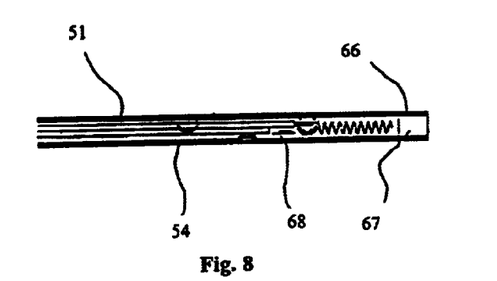
FIG. 8 is a detailed sectional view of the distal extremity of the probe shown in FIG. 5.
Figure 9:
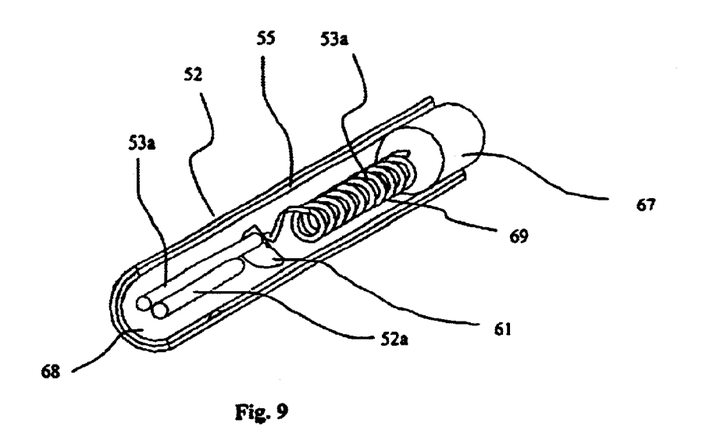
FIG. 9 is an enlarged isometric view of the distal extremity of the probe shown in FIGS. 5 and 6 with certain parts being broken away.

As shown in FIG. 6, one end of the cable 31 extends into the recess 48. A cylindrical cannula 51 is secured within the other end of the probe hub 46. A plurality of conductors of at least two as for example two conductors 52 and 53 (see FIG. 4) are disposed in a lumen 54 in a sheath 55 forming the cannula 51. The sheath 55 is formed of a suitable polymer such as a polyimide or Teflon. The conductors 52 and 53 are provided with insulation 56. The conductors 52 and 53 are connected to the conductors 32 and 33 within the recess in a suitable manner such as solder joints (not shown) after which the recess 47 can be filled with a suitable material such as an adhesive (not shown).

The conductor 52 can be in the form of a platinum wire having a size ranging from 0.001 to 0.008" in diameter and the conductor 53 can be formed of silver also having a diameter of 0.001 to 0.008" in diameter. The cannula 51 is of a small outside diameter smaller than 20 gauge medical and thus has an outside diameter ranging from 0.4 to 0.8 mm and preferably a diameter of approximately 0.5 mm. The sheath 55 of the cannula 51 can have a wall thickness ranging from 0.02 to 0.075 mm and preferably a diameter of 0.25 mm. The cable 31 can have a suitable length as for example approximately 24" whereas the cannula 51 can have a suitable length as for example approximately 3".

One or more but at least one window 61 is provided in the cannula 51 which can be in the form of an oval-shaped opening as shown (see FIG. 7) extending longitudinally of the sheath 55 of the cannula 51. The oval-shaped window or windows are disposed in the distal extremity of the cannula 51 and are positioned in appropriate positions as hereinafter described. The windows or openings 61 are covered with a coating 62 which is permeable to oxygen and formed of a suitable material such as a silicone or a polyethylene which forms a coating extending along the length of the exterior of the sheath 55 of the cannula 51. The openings or windows 61 throughout are spaced apart longitudinally and circumferentially of the sheath 55 of the cannula 51. The platinum and silver conductors form an electrode assembly 64 which serves as an oxygen sensor as hereinafter described.

The cannula 51 is provided with a tip 66 which is filled with a cylindrical plug 67 formed of a suitable polymeric material and secured in place by suitable means such as an adhesive (not shown). The space in the lumen 54 within the sheath 55 of the cannula 51 extending proximally from the plug 67 is filled with a suitable buffer solution 68 such as potassium chloride. The first or platinum and the second or silver electrodes 52 and 53 forming the electrode assembly for the oxygen sensor of the present invention are disposed in this buffer solution 68 and consists of the platinum conductor 52 which has a distal extremity 52a of a suitable diameter as for example 0.002" to 0.022" and has a length which is free of insulation of 0.050 to 0.3". The silver electrode 53 also extends into the buffer solution 68 and has a distal extremity 53a which is free of insulation and which has a suitable diameter as for example 0.002". The distal extremity 53a has been coiled into a helical coil 69 to maximize the surface area of the silver which is in contact with the buffer solution 68. This portion 53a is coated with a silver chloride to a thickness of approximately 0.001". By the use of this silver coil it is possible to increase the surface area of the silver chloride in contact with the buffer solution by at least three times. The length of the coil 69 can range from 1/16" to 1/8". This silver coil 69 should be separated from the platinum electrode 52a by a suitable distance as for example 0.03 to 0.2".

The platinum serves as a catalyst for the chemical reaction which generates an electrical current in the nano-ampere range that is supplied through the conductors 52 and 53 in the cannula 51 to the conductors 32 and 33 in the cable 31. In order to maintain accurate readings of current flow, the amount of platinum exposed is kept to a minimum while maximizing the silver and silver chloride exposure to the buffer solution 68. In order to prevent the buffer solution from creeping up under the insulation of the platinum wire and to thereby control the amount of platinum which is exposed as a catalyst to the buffer solution, the distal extremity 52a of the platinum conductor 52 is inserted into a small capillary tube of a suitable material such as glass. The insulated platinum is disposed in the tube so that only the distal bare extremity is exposed. An adhesive is then placed in the capillary tube and cured under heat. After the adhesive cured, a cut can then be made through the wire without upsetting the mechanical integrity of the insulation. This provides an insulated wire with a very clean cut distal end into which the buffer solution cannot creep.

In preparation of the coil of the silver wire, the wire can be mounted on a mandrel as for example a mandrel having a diameter of 0.05". This coil then can be dipped into molten silver chloride which ablates the insulation on the exterior of the coil and coats this surface with silver chloride.

By constructing the electrode assembly 64 in this manner, it is possible to make the probe small enough so that it can be readily inserted into a vein or artery in a patient's forearm and not obstruct the normal flow of blood. At the same time it is possible to maximize the surface area of the silver wire which is coated with silver chloride in contact with the potassium chloride solution.

This electrode assembly hereinbefore described is disposed a distal 3/4" and preferably a distal 1/2" of the cannula 51. This distal extremity can have at least one and preferably two or more of the windows or openings 61 which are coated with the thin coating of silicone as hereinbefore described which is very permeable to oxygen. This coating preferably has a thickness ranging from 0.0005" to 0.003" and preferably a thickness of approximately 0.001". These windows allow communication of the oxygen in the blood through the silicone membrane 62 into the potassium chloride buffer solution 63 in the lumen 54 inside the cannula 51.

The windows 61 can range in length from 1/2 mm to 2 mm with a width of 1/4 mm. The membrane on the windows can be formed by placing a Teflon mandrel within the cannula and dipping the distal extremity of the cannula 51 in a silicone dispersion solution and thereafter allowing it to cure with the mandrel in place. Thereafter after curing, the Teflon mandrel can be removed leaving the silicone coating 62 on the cannula. Alternatively the distal extremity of the probe can be a single window in the form of an annulus (not shown) 1/2 millimeter to 1 centimeter formed by a tube of gas permeable material such as a silicone or a polyethylene with the distal tip being sealed or plugged.

The electrode assembly 64 is placed in the desired position within the lumen 54 in the cannula 51, after which the cannula can be filled with the buffer solution 63 and then plugged at the distal end with a tip plug 67. Alternatively the electrode assembly 64 after it has been prepared is loaded from the proximal end of the cannula 51 and is moved into the distal end, stopping near the tip plug being previously inserted and the lumen 54 filled with the buffer solution 68 with the platinum electrode in close proximity to one of the windows 61. The cannula 51 with the electrode assembly 64 disposed in the buffer solution 68 in the lumen 54 is then sealed with an adhesive (not shown) on the proximal end and then mounted in the hub 43 with the conductors 52 and 53 being soldered to the conductors 32 and 33 of the cable 31.

Figure 10:
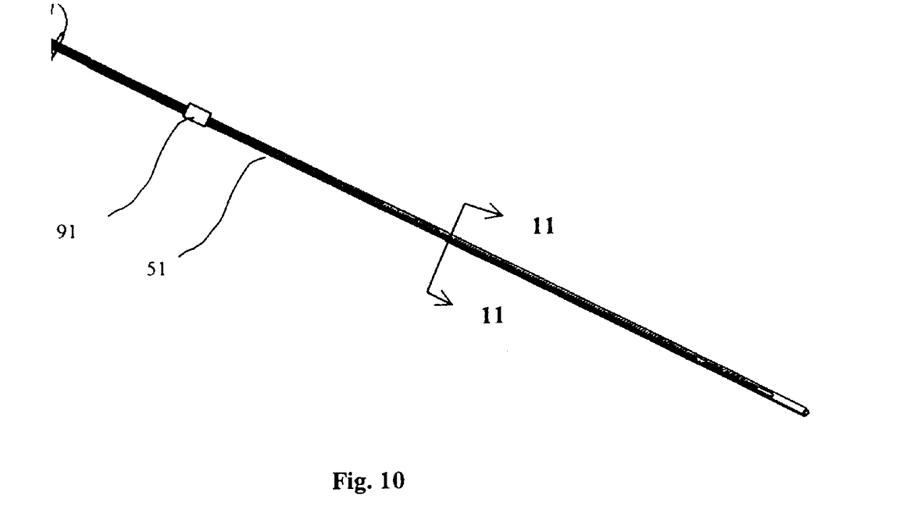
FIG. 10 is an enlarged view of the distal extremity of another embodiment of a probe incorporating the present invention.
Figure 11:
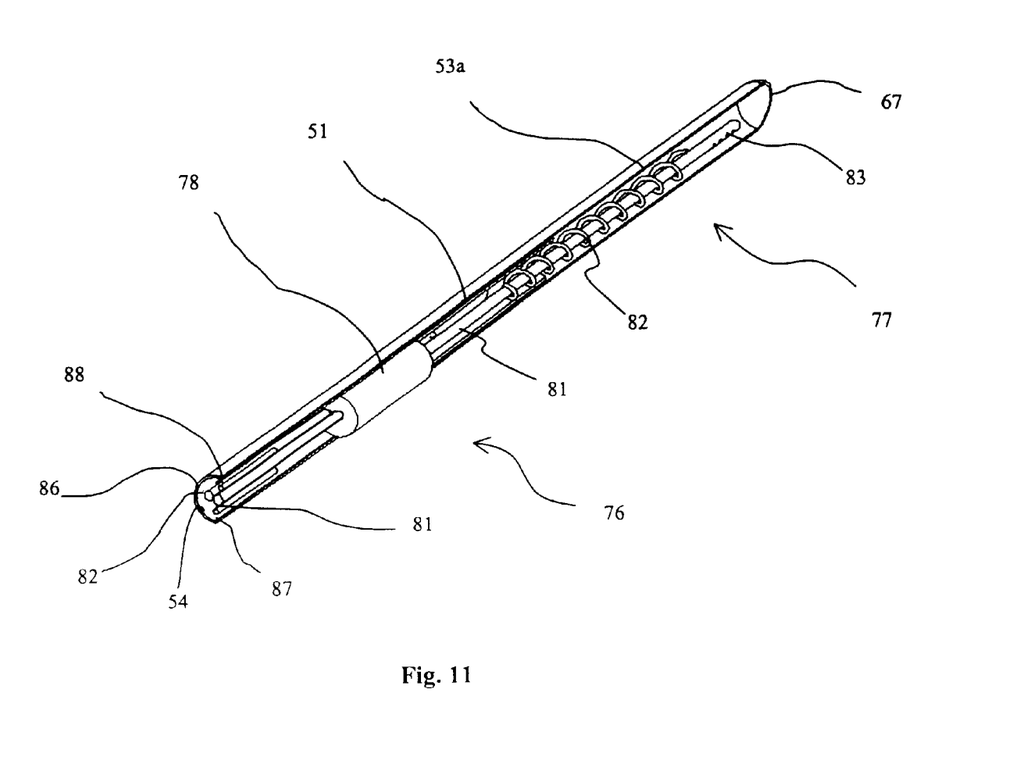
FIG. 11 is a detailed sectional view of the distal extremity of the probe shown in FIG. 8.
Figure 12:
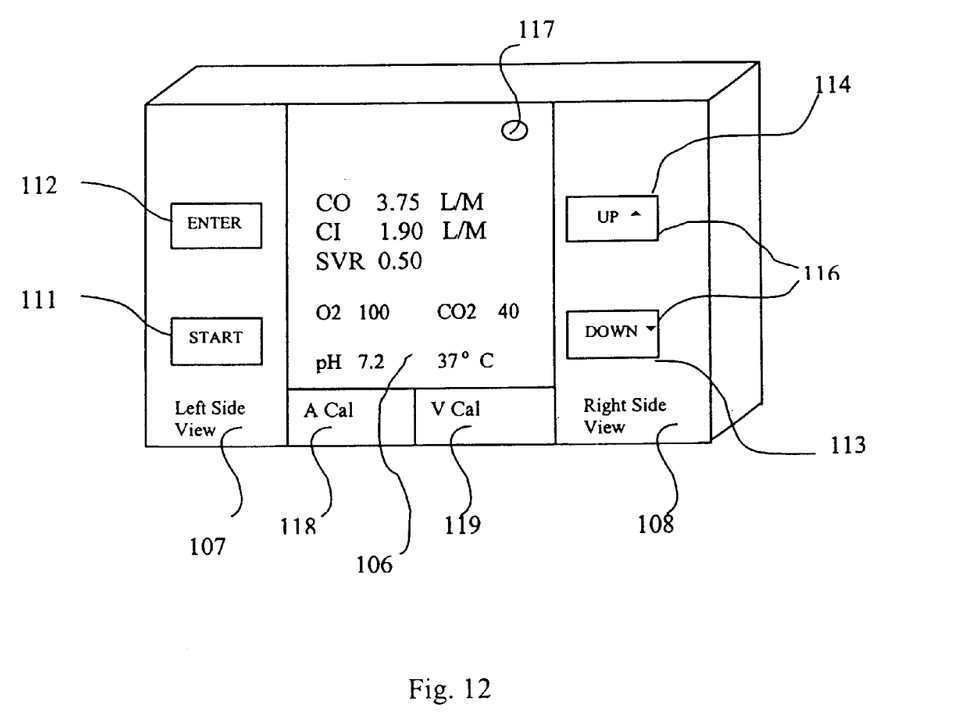
FIG. 12 is a schematic representation of the front and left and right sides of the control and display module.

In the event it is desired to utilize the probe 23 or 24 for other purposes in addition to sensing oxygen as for example for sensing carbon dioxide or blood pH, a secondary or additional sensor assembly 76 can also be provided in the sheath 55 of the cannula 51. Thus as shown in FIGS. 10 and 11, the secondary sensor assembly 76 is positioned proximal of the primary or oxygen sensor assembly 77 corresponding to the oxygen sensor assembly 21 hereinbefore described. There is provided a barrier plug 78 within the lumen 54 of the sheath 55 in the form of a disk which seals an alternative embodiment of an electrode assembly serving as an oxygen sensor in the buffer solution contained therein from the secondary sensor assembly 76 proximal thereof.

The alternative embodiment of the oxygen sensor shown in FIGS. 10 and 11 is an electrode assembly 77 and consists of first and second conductors 81 and 82 in which the first conductor is formed of platinum and is covered by an insulating layer of glass in the manner hereinbefore described. The distal extremity of the conductor 81 rather than being provided with a bare distal extremity as for the conductor 52 is covered entirely by glass and is sealed with an adhesive but to provide a controlled exposure of the platinum, at least one and preferably a plurality of microscopic holes 83 are provided within the glass insulation by the use of laser to expose minute areas of the platinum in the order of 4 $\mu$m to 0.02" in diameter. A shown, the holes 83 can be spaced apart longitudinally of the glass insulation at the distal extremity of the first conductor 81. The second conductor 82 is formed of silver and coated with silver chloride in the same manner as the conductor 53. The distal extremity of the second conductor 82 is wound in a helix and extends over the conductor 81 so that the conductor 81 extends through the helix and beyond the helix so that the holes 83 are disposed distal of the helix. The conductors 81 and 82 are disposed in a buffer solution 68 of the type hereinbefore described which fills the space between the tip plug 67 and the plug 78. The conductors 81 and 82 extend through the plug 78 and are connected in the same manner as conductors 52 and 53 to the proximal extremity of the cannula 51. The operation of the oxygen sensor assembly 77 is very similar to that hereinbefore described for the sensor assembly 21. However, the use of the precision holes 83 formed in the glass layer and opening up the platinum for exposure makes it possible to more precisely quantify the area of platinum exposed to the buffer solution.

As a part of the secondary sensor assembly 76, a secondary sensor buffer solution 86 is provided in the space in the lumen 54 proximal of the plug 82 and also can be potassium chloride. The secondary sensor assembly 76 also includes a secondary sensor anode wire 87 in the form of silver wire coated with silver chloride. A cathode 88 is provided which is formed of platinum wire coated with platinum oxide. As can be seen, the platinum and silver conductors 81 and 82 extend through the second buffer solution 86 but are insulated so they do not react with the buffer solution used for the secondary sensing assembly 86. Additional conductors (not shown) are provided which are connected to the silver anode 87 and the platinum cathode 88 and are connected to corresponding conductors (not shown) carried by the cable 31.

The coating 62 hereinbefore described must include a coating which allows diffusion of gases $O_2$ and $CO_2$. One such coating found particularly satisfactory for allowing such diffusion is MED10-6605 silicone elastomer (NuSil Silicone Technology). This silicone coating also in accordance with the present invention should include a coating applied thereover which is anti-thrombogenic and which is compatible with silicone. The coating in addition to being anti-thrombogenic should be lubricious to ensure that the cannula 51 can be readily introduced as hereinafter described and is compatible with blood to provide flawless continuous functioning of the sensors without impediment of thrombins.

An insertion marker band 91 is placed on the cannula 51 to provide an indication on the cannula when the cannula 51 has been inserted to the proper depth.

The control and display module 22 as shown in FIG. 1 which forms a part of the apparatus 21 of the invention consists of a housing 101 formed of a suitable material such as plastic and which is sized so it can be held in the human hand. It is provided with an LCD display 102 which is readily visible to the user. It is provided with input pads or keys hereinafter described to facilitate the entry of data and to control the display on the LCD display 102. It is also provided with electrical connectors of the type hereinbefore described (not shown) into which the probes 23 and 24 can be coupled.

The housing 101 is provided with a front side 106 which has the LCD display 102 mounted therein. It is also provided with a left side 107 and right side 108 which are shown schematically in FIG. 11. It is also provided with a bottom side 109 onto which the probes 23 and 24 are mounted. As shown, the left hand side 107 is provided with start and enter push buttons 111 and 112 and the right hand side 108 is provided with down and up push buttons 113 and 114. Lighted arrows 116 are provided on the push buttons 113 and 114. A green light 117 is provided on the front side 106 and is lit when the controller is turned on by operation of the start push button 111. The display 102 is provided with a plurality of text fields of which only one is visible at a time, reflecting the mode that the control and display module is operating in. For example text fields are provided for entering HCT, weight, height, and inspired oxygen ($O_2$) between the "3.75 l/m" and the smaller ($O_2$) and ($CO_2$) which are provided pH and temperature in degrees Centigrade. There are provided arterial and venous calibration pushbuttons 118 and 119.

Figure 13:
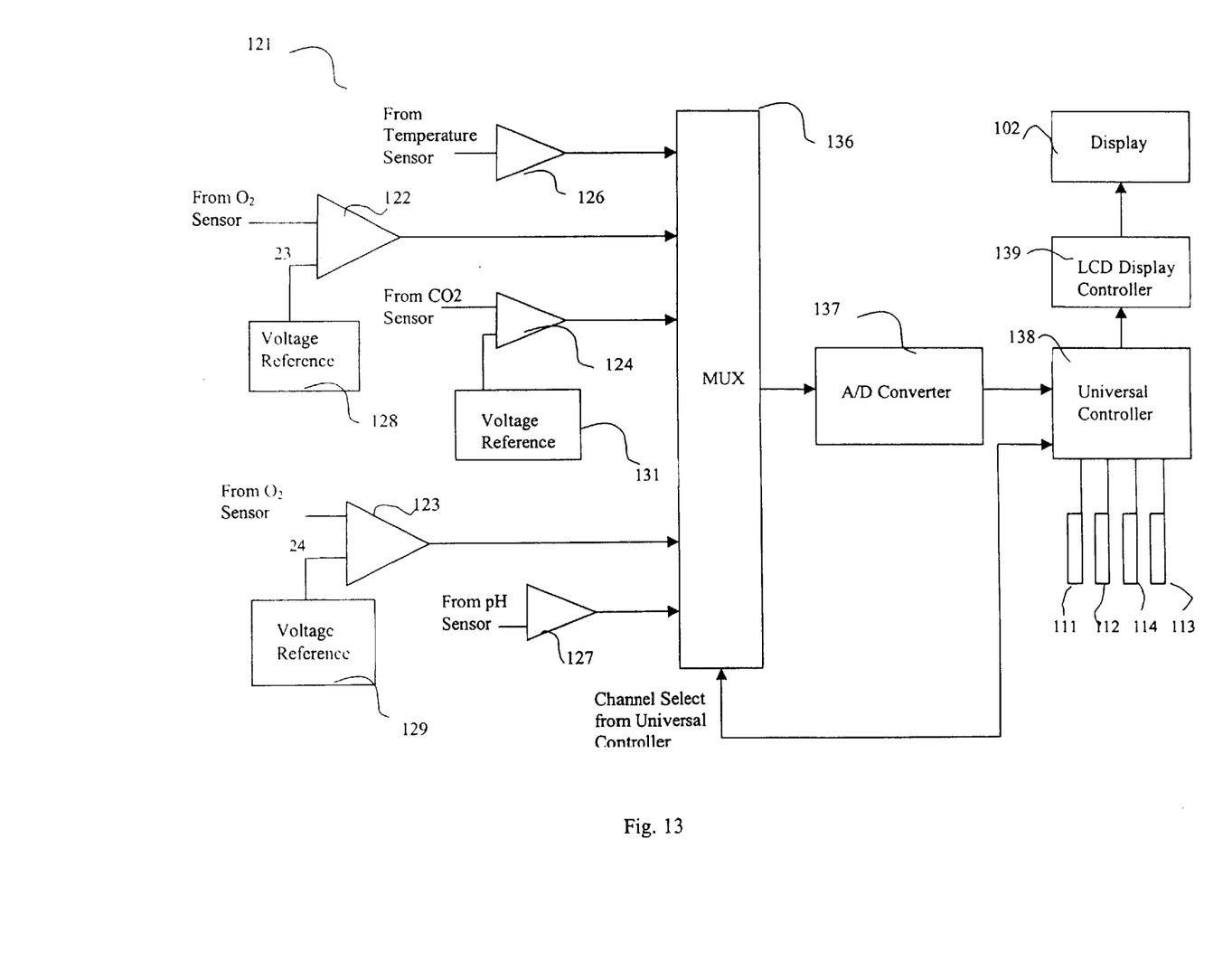
FIG. 13 is a block diagram of the electronics which are incorporated in the control and display module.

The electronics 121 provided in the control and display module 22 is shown in block diagram form in FIG. 13. As shown therein, the electronics 121 consists of a plurality of current to voltage preamplifiers 122, 123, 124, 126 and 127 with one preamplifier being provided for each of the sensors. Thus as shown, a preamplifier 122 is provided for the oxygen sensor probe 23 and a preamplifier 123 is provided for the oxygen sensor for the probe 24. A preamplifier 124 is provided for the $CO_2$ sensor and similarly a preamplifier 126 is provided for the temperature sensor and preamplifier 127 is provided for the pH sensor. Precision voltage references 128, 129, and 131 are provided respectively for the preamplifiers 122, 123 and 124. As shown in FIG. 13, the outputs of the preamplifiers 122, 123, 124, 126 and 127 are supplied to a multiplexer 136 which supplies the outputs from the probes individually and one by one to an A/D converter 137. The A/D converter can be of a suitable type such as a Max 111. The output of the A/D converter 137 is supplied to controller 138 which can be of a suitable type such as an ATMEL 90S2313 that serves as a microprocessor. The start and enter push buttons 111 and 112 are connected thereto as are the down and up push buttons 113 and 114 as shown. The controller 138 is connected to an LCD display controller 139 which can be of a suitable type such as the Phillips 8576. The LCD display controller is connected to the LCD display 102 which is visible from the front side 106 of the housing 101 of the control and display module 22.

The electronics hereinbefore described in FIG. 11 is operable from two non-rechargeable button cell batteries to provide ±1.5 volt operation. The circuitry provides a low battery drain and has self-testing characteristics.

Although in the electronic circuitry shown in FIG. 11, the preamplifiers, the voltage references, the multiplexer and the A/D converters have been shown incorporated therein within the housing 101 of the control and display module 22, if desired, the preamplifiers, the voltage references, the multiplexer and the A/D converters can be incorporated in the probes themselves because they are capable of being miniaturized without any significant enlargement of the probes. The probes and the electronics associated therewith have been designed to greatly reduce or minimize 60 Hz magnetic and capacity pickup for all measurements being made by the probes. A responsivity of 1 sec maximum time constant for all channels of the probes is provided. For the oxygen measurement in the blood, two channels have been provided by the two probes 23 and 24, providing outputs ranging from 0 to 20 nanoamperes. The precision voltage reference can be −0.7 volts ±50 millivolts to provide the constant voltage required by the probes 23 and 24 for their operation. As shown, only one probe is required for the $CO_2$ measurement and similarly only one probe is required for the pH measurements. Accuracy and linearity are within 5%.

Operation and use of an apparatus of the present invention as herein disclosed for performing the method of the present invention may now be briefly described as follows. Let it be assumed that the patient on which the apparatus and method is to be utilized has a compromised cardiac output because of prior heart muscle damage and it is desired to ascertain the efficacy of the heart by ascertaining cardiac output to optimize therapy for the patient as for example for prescribing appropriate drug or drugs. The apparatus of the present invention is designed to measure a cardiac output using the so-called gold standard ($AVO_2$) differential equation which is the underlying equation for the Fick cardiac output method.

The patient to be examined is placed in a stable resting position as for example lying in a bed or sitting in a chair. The control module 22 can be set up. The patient's hemoglobin is inserted into the control module 22 by pressing the appropriate button. The control module will default to an HGB of 12 if no value is entered. The patient's height, weight, and arterial pressure are also inserted into the control module 22 by pressing appropriate buttons. The selected forearm 26 of the patient is then prepared by swabbing the skin with an appropriate disinfectant. Before the venous probe insertion, a tourniquet is placed on the upper portion of the arm. A vein in the forearm is then cannulated utilizing a conventional split-sheath-covered insertion needle. After the vein has been accessed, the needle is removed from the sheath while leaving the sheath in situ. The venous probe 24 is then taken and the cannula 51 thereof inserted into the sheath and introduced into the vein up to the insertion marker band 91. The sheath is then carefully removed by sliding it back from the cannula 51 without dislodging the cannula and thereafter the split sheath is split apart and removed from the venous probe 24. The venous probe is then secured to the patient's forearm with a suture or tape (not shown).

Thereafter the radial brachial artery of the same forearm can be cannulated utilizing another split-sheath-covered insertion needle. After the artery has been accessed, the needle can be removed leaving the sheath in situ. The arterial probe 23 is then taken and inserted through the sheath up to the insertion marker band 91. The split sheath is then removed from the arterial probe 23 by pulling it back out of the artery while not dislodging the arterial probe. The split sheath is then pulled to split it apart and remove it from the arterial probe. The arterial probe 23 is then secured to the forearm 26 with a suture or tape.

The electrical connectors 41 of the arterial and venous probes 23 and 24 are inserted into the appropriate electrical connectors in the control module 22. The control module 22 is then attached to the patient's upper arm 27 with the Velcro-backed armbands 28.

After these procedures have been completed, the patient is instructed to keep the instrumented arm still for three minutes prior to commencing cardiac output calculations utilizing the present invention to ensure accuracy of the measurements. As soon as the patient's arm has been at rest for this period of time, the start push button 111 of the control and display unit 22 can be depressed to cause the green light to be lit to indicate that a command has been received to measure blood gas and calculate cardiac output of the patient. Thereafter, the green light will blink slowly and cardiac output, $O_2$, $CO_2$ and pH and temperature will be displayed on the screen or LCD display 102 of the control module. After thirty seconds the screen will return to its unlit state and the green light turns off. If the operator needs to check the last five cardiac outputs recorded, the start push button can be pressed successively to ascertain a trend.

In addition, a printed record can be provided by utilizing the print-out port provided on the control module and connecting the same to an appropriate printer.

After the desired measurements have been made, the apparatus 21 can be removed from the patient by removing the module 22 and removing the probes from the forearm 26 and closing the openings in an appropriate manner by pressing on a vessel or vessels and placing appropriate seals over the openings into the vessels.

The electronics hereinbefore described has incorporated therein a computer in the form of a microprocessor which is provided with software that includes an algorithm for the $AVO_2$ differential equation well known to those skilled in the art which has been modified in accordance with the present invention to include an adjustment factor or a standard variance which represents a comparison from mixed venous blood in the pulmonary artery of the patient and the blood in a vein in the forearm of the patient. In the $AVO_2$ differential equation, a mixed venous sample is utilized which is drawn from the pulmonary artery of the patient. This modified $AVO_2$ equation can be represented as follows:

Arterial partial pressure of $O_2$ minus venous partial pressure of $O_2$ (adjusted for variance between pulmonary artery and venous forearm)

$O_2$ consumption is estimated as 3 ml $O_2$/kg. $O_2$ content equals saturation×1.36×hemoglobin.

The standard (O$_2$ consumption) cardiac output formula is:

$$\text{Cardiac Output} = \frac{O_2 \text{ consumption (ml/min)}}{AVO_s \text{ difference (ml } O_2/100 \text{ ml blood)} \times 10}$$

Cardiac Index is calculated by dividing the cardiac output by the body surface area. Systemic vascular resistance may also be calculated if desired.

From the foregoing it can be seen that the apparatus and method of the present invention makes it possible to measure cardiac output of a patient as well as other parameters of the patient including carbon dioxide, temperature and pH. As hereinbefore described, one intra-arterial probe include three sensors: an O$_2$ sensor, a carbon dioxide sensor and a pH sensor. These sensors are included in a cannula which is of a very small diameter of less than 20 gauge so it can be readily inserted into venous and arterial vessels in the forearm. A continuous in vivo cardiac output is obtained utilizing a modified arterial/venous differential equation. Measurements are accurate to ±3% with minimal drift over 72 hours. The probes utilized are blunt and atraumatic to the vessel wall and are coated with anti-thrombogenic substances to inhibit clotting, eliminating the need for an IV drip to maintain a clot-free environment. The response time of the sensors in the probes is less than 5 minutes.

What is claimed:

1. Apparatus for ascertaining cardiac output of the heart of a patient having arteries having arterial blood therein supplied by the heart and veins having venous blood therein being returned to the heart which extend into a forearm of the patient comprising a control and display module, a venous probe adapted to be inserted into a vein in the forearm of the patient and coupled into the control and display module and providing an electrical signal representing the dissolved oxygen in the venous blood in the vein, an arterial probe adapted to be inserted into an artery in the forearm of the patient and coupled into the control and display module for providing an electrical output signal representing the dissolved oxygen in the arterial blood in the artery, the control and display module having a visible display, the control and display module having electronics therein including a microprocessor for receiving the electrical output signals from the venous probe and the arterial probe and providing a continuous in vivo cardiac output on the display and utilizing in connection therewith an arterial venous oxygen differential equation which includes an adjustment factor for adjusting for venous blood being sampled in the forearm of the patient rather than mixed venous blood in the pulmonary artery of the patient.

2. Apparatus as in claim 1 in which each probe is provided with a cannula having an outside diameter of less than 20 gauge to facilitate its ready insertion into the veins and arteries of the forearm of the patient.

3. Apparatus as in claim 1 wherein each of said venous probe and arterial probe is comprised of a hub, a cannula mounted in the hub, an oxygen sensor assembly mounted in the cannula, the cannula having an opening therein overlying the oxygen sensor assembly, an oxygen permeable membrane covering said opening in said cannula, said oxygen sensor assembly including a buffer solution disposed in the cannula and first and second electrodes disposed in the buffer solution and providing an electrical output, means connecting the sensor assembly and supplying the electrical output through the cannula to the hub and a conducting cable connected to the electrical conductors in the hub and to the control and display module.

4. Apparatus as in claim 1 wherein the hub of each of said probes is provided with a wing facilitating grasping of the hub to facilitate introduction of the cannula by the use of the hub.

5. Apparatus as in claim 1 wherein said cannula on each of said probes has an outside diameter of less than 20 gauge to facilitate introduction of the cannula into the veins and arteries of the forearm of the patient.

6. Apparatus as in claim 1 wherein at least one of said probes is provided with an additional sensor assembly disposed in the cannula proximal of the oxygen sensor in the cannula and providing an electrical output and means in the cannula for isolating the additional sensor assembly from the oxygen sensor assembly so that one sensor assembly does not interfere with the measurements being made by the other sensor assembly, the cannula having an opening overlying the additional sensor assembly and an oxygen permeable membrane covering said additional opening in the cannula.

7. Apparatus as in claim 6 wherein said oxygen sensor assembly includes an electrode that has been coiled to maximize contact with the buffer solution.

8. A probe for use in ascertaining cardiac output and other parameters in connection with a control and display module comprising a cannula, an oxygen sensor assembly mounted in the cannula, the cannula being gas permeable in the vicinity of the oxygen sensor assembly, said oxygen sensor assembly including a buffer solution disposed in the cannula and first and second electrodes disposed in the buffer solution and providing a first electrical output, a carbon dioxide sensor assembly disposed in the cannula proximal of the oxygen sensor assembly, the cannula being gas permeable in the vicinity of the carbon dioxide sensor assembly, the carbon dioxide sensor assembly providing a second electrical output, means for isolating the carbon dioxide sensor assembly from the oxygen sensor assembly so that the measurements of one sensor assembly do not interfere with the other sensor assembly and conductor means connected to the oxygen sensor assembly and to the carbon dioxide sensor assembly and supplying the first and second electrical outputs through the cannula to the control and display module.

9. A probe as in claim 8 wherein one of said first and second electrodes is provided with a coiled distal extremity to maximize contact with the buffer solution.

10. A probe as in claim 8 further comprising a hub, the cannula being mounted in the hub and the hub being provided with a wing adapted to be grasped by fingers of the hand to facilitate insertion of the probe into an artery or vein in the forearm of the patient.

11. A probe as in claim 8 wherein said cannula has an outside diameter of less than 20 gauge.

12. A probe for use in ascertaining cardiac output and other parameters in connection with a control and display module comprising a cannula, an oxygen sensor assembly mounted in the cannula, said oxygen sensor assembly including a buffer solution disposed in the cannula and first and second electrodes disposed in the buffer solution and providing an electrical output, one of the first and second electrodes being provided with a coiled distal extremity to maximize contact with the buffer solution, conductor means connected to the sensor assembly and supplying the electrical output through the cannula to the control and display module.

13. A probe as in claim 8 wherein said cannula is formed of a plastic.

14. A method for ascertaining cardiac output of the heart of a patient having arteries having arterial blood therein supplied by the heart and veins having venous blood therein being returned to the heart which extend into a forearm of the patient comprising the steps of providing an electrical signal representing the dissolved oxygen in the venous blood in a vein of the forearm of the patient, providing an electrical signal representing the dissolved oxygen in the arterial blood in an artery in the forearm of the patient, using the electrical signals to provide a continuous in vivo cardiac output by utilizing an arterial venous oxygen differential equation which includes an adjustment factor for adjusting for venous blood being sampled in the forearm of the patient rather than in the mixed venous blood in the pulmonary artery of the patient.

15. A method as in claim 14 further including the steps of providing additional measurements from the venous and arterial blood in the vein in the forearm of the patient.

* * * * *